(12) United States Patent
Sabbadini

(10) Patent No.: US 6,534,322 B1
(45) Date of Patent: Mar. 18, 2003

(54) KITS FOR EARLY DETECTION OF HEART DISEASE

(75) Inventor: Roger A. Sabbadini, Lakeside, CA (US)

(73) Assignee: Medlyte Diagnostics, Inc., San Diego, CA (US)

(*) Notice: Subject to any disclaimer, the term of this patent is extended or adjusted under 35 U.S.C. 154(b) by 0 days.

(21) Appl. No.: 09/489,158

(22) Filed: Jan. 21, 2000

Related U.S. Application Data

(62) Division of application No. 09/084,069, filed on May 22, 1998, now Pat. No. 6,210,976.
(60) Provisional application No. 60/049,274, filed on Jun. 10, 1997.

(51) Int. Cl.$^7$ ............................................. G01N 33/543
(52) U.S. Cl. ..................... 436/518; 435/7.1; 435/7.92; 435/810; 435/967; 435/975; 436/71; 436/63; 436/536; 436/541; 436/161; 436/162; 436/173; 436/808; 530/412; 530/413; 530/417
(58) Field of Search ................... 435/7.1, 7.92, 435/810, 967, 975; 436/71, 63, 518, 536, 541, 161, 162, 173, 808; 530/412, 413, 417

(56) References Cited

U.S. PATENT DOCUMENTS

| | | | |
|---|---|---|---|
| 4,376,110 A | | 3/1983 | David et al. ............... 436/513 |
| 5,223,409 A | | 6/1993 | Ladner et al. ............. 435/69.7 |
| 5,290,678 A | | 3/1994 | Jackowski .................. 435/7.4 |
| 5,331,093 A | * | 7/1994 | Ishihara et al. .......... 530/387.5 |
| 5,403,484 A | | 4/1995 | Ladner et al. ........... 435/235.1 |
| 5,604,105 A | | 2/1997 | Jackowski .................. 435/7.4 |
| 5,710,008 A | | 1/1998 | Jackowski .................. 435/7.4 |

OTHER PUBLICATIONS

Sigma Catalog, 1992, p. 1152.*
Cordis et al, HPTLC analysis of sphingomylein, ceramide, & sphingasine in . . . , 1998 16, Journal of Pharmaceutical & Biomedical Analysis, pp. 1189–1193.*
Cuturi et al., "Independent Regulation of Tumor Necrosis Factor and Lymphotoxin Production by Human Peripheral Blood Lymphocytes," *J. Exp. Med.* 165, 1581–1594 (1987).
Cuvillier et al., "Suppression of Ceramide–Mediated Programmed Cell Death by Sphingosine–1–Phosphate," *Nature* 381, 800–803 (1996).
Deng et al. "Arterial and venous cytokine response to cardiopulmonary bypass for low risk CABG and relation to hemodynamics," *Eur. J. Cardiol.* 9:22–29 (1995).
Dettbarn et al., "Modulation of Cardiac Sarcoplasmic Reticulum Ryanodine Receptor by Sphingosine," *J. Mol. Cell Cardiol.* 26:229–242 (1994).
Faucher et al., "Regulation of the Epidermal Growth Factor Receptor Phosphorylation State by Sphingosine in A431 Human Epidermoid Carcinoma Cells," *J. of Biol. Chem.* 263(11):5319–5327 (1988).
Franson et al., "Sarcoplasmic Reticulum Dysfunction: Phospholipid Alterations Induced by Lysosomal Phospholipase C" *Am. J. of Phys. Soc.* H1017–1023 (1986).

(List continued on next page.)

*Primary Examiner*—Christopher L. Chin
(74) *Attorney, Agent, or Firm*—Foley & Lardner; Richard J. Warburg

(57) ABSTRACT

The invention relates to methods, compositions, kits, and devices for detecting cardiac ischemia, hypoxia, or other causes of heart failure in a mammal by obtaining a test sample from a mammal, measuring a level of a non-polypeptidic cardiac marker in the test sample, and determining if the level of the cardiac marker measured in said test sample correlates with cardiac ischemia or hypoxia or another form of heart failure.

16 Claims, 1 Drawing Sheet

OTHER PUBLICATIONS

Giroir et al., "Inhibition of Tumor Necrosis Factor Prevents Mycocardial Dysfunction During Burn Shock", *Am. Physiol. Soc.* 267:H118–H124 (1994).

Giroir et al., "The Tissue Distribution of Tumor Necrosis Factor Biosynthesis during Endotoxemia", *J. Clin. Invest.* 90:693–698 (1992).

Gottlieb et al., "Cell Acidification in Apoptosis: Granulocyte Colony–Stimulating Factor Delays Programmed Cell Death in Neutrophlis by Up–Regulating the Vacuolar $H^+$–ATPase" *Proc. Natl. Acad. Sci. USA* 92:5965–5968 (1995).

Grob et al., "The Chemistry of Sphingosine" *Record of Chem. Progress* 18(2):55–66 (1957).

Gurevitch et al., "Tumor Necrosis Factor–Alpha Is Released From the Isolated Heart Undergoing Ischemia and Reperfusion," *JACC* 28(1) 247–252 (1996).

Hannun et al., "Lysosphingolipods Inhibit Protein Kinase C: Implications for the Sphingolipdoses," *Science* 235:670–674 (1987).

Hannun et al., "Sphingosine Inhibition of Protein Kinase C Activity and of Phorbol Dibutyrate Binding In Vitro and In Human Platelets" *J. of Biol. Chem.* 261(27):12604–12609 (1986).

Hennein et al., "Cardio–Thoracic and Vascular Surgery: New Techniques in Myocardial Protection I" *Supplement to Circulation: Abstracts from the 66$^{th}$ Scientific Sessions* 88(4) part 2:I–247 (1993).

Hennein et al., "Relationship of the Proinflammatory Cytokines to Myocardial Ischemia and Dysfunction After Uncomplicated Coronary Revascularization" *J. of Thoracic and Cardiovas. Surgery* 108(4):626–635 (1994).

Herskowitz et al., "Cytokine mRNA Expression in Postischemic/Reperfused Myocardium," *Am. J. of Pathology* 146:419–428 (1995).

Horokko et al., "Antiphospholipid Antibodies Are Directed Against Epitopes of Oxidized Phospholipids" *J. Clin. Invest.* 98(3):815–825 (1996).

Hurley et al., "Taxonomy and Function of C1 Protein kinase C Homology Domains," *Protein Science* 6:477–480 (1997).

Jozwiak et al., "Lactosylsphingosine–Reactive Antibody and CEA in Patients with Colorectal Cancer" *Eur. J. Cancer Clin. Oncol.* 18(7):617–621 (1982).

Kajstura et al., "Apoptotic and Necrotic Myocyte Cell Deaths are Independent Contributing Variables of Infarct Size in Rats" *Lab. Invest.* 74(1):86–107 (1996).

Kelker et al., "Characterization of Human Tumor Necrosis Factor Produced by Peripheral Blood Monocytes and Its Separation From Lymphotoxin" *Int. J. Cancer* 36:69–73 (1985).

Kohler et al., "Continuous Cultures of Fused Cells Secreting Antibody of Predefined Specificity", *Nature* 256:495–497 (1975).

Kramer et al., "Endothelin and Increased Contractility in Adult Rat Ventricular Myocytes: Role of Intracellular Alkalosis Induced by Activation of the Protein Kinase C–Dependent $Na^+$–$H^+$ Exchanger" *Circulation Research* 68(1):269–271 (1991).

Krown et al., "TNFα Receptor Expression in Rat Cardiac Myocytes: TNFα Inhibition of L–Type $Ca^{2+}$ Current and $Ca^{2+}$ Transients" *FEBS Letters* 376:24–30 (1995).

Krown et al., "Tumor Necrosis Factor Alpha–Induced Apoptosis in Cardiac Myocytes" *J. Clin. Invest.* 98(12):2854–2865 (1996).

Kubota et al., "Accumulation of Ceramide in Ischemic Human Brain of an Acute Case of Cerebral Occlusion" *Japan J. Exp. Med.* 59(2):59–64 (1989).

Kuziemko et al., "Cholera Toxin Binding Affinity and Specificity for Gangliosides Determined by Surface Plasmon Resonance" *Biochem.* 35:6375–6384 (1996).

Lefer et al., "Mediation of Cardioprotection by Transforming Growth Factor–β" *Science* 249:61–64 (1990).

Leiberman et al., "Production of Tumor Necrosis Factor and Other Cytokines by Astrocytes Stimulated with Lipopolysaccharide or a Neurotropic Virus" *Proc. Natl. Acad. Sci. USA* 86:6348–6352 (1989).

Lindemann et al., "Granulocyte–Macrophage Colony–Stimulating Factor Induces Cytokine Secretion by Human Polymorphonuclear Leukocytes" *J. Clin. Invest.* 83:1308–1312 (1989).

Levine et al., "Elevated Circulating Levels of Tumor Necrosis Factor in Severe Chronic Heart Failure" *New Eng. J. of Med.* 323(4):236–241 (1990).

Libby et al., "Edotoxin and Tumor Necrosis Factor Induce Interleukin–1 Gene Expression in Adult Human Vascular Endothelial Cells" *AJP* 124:179–185 (1986).

Lowe et al., "Sphingosine Differentially Inhibits Activation of the $Na^+$/$H^+$ Exchanger by Phorbol Esters and Growth Factors" *J. Biol. Chem.* 265(13):7188–7194 (1990).

Mair et al., "Equivalent Early Sensitivities of Myoglobin, Creatine Kinase MB Mass Cratine Kinase Isoform Ratios and Cardiac Troponins I and T for Acute Myocardial Infarction" *Clin. Chem.* 41(9):1266–1272 (1995).

Maury et al., "Circulating Tumor Necrosis Factor–α (Cachectin) in Myocardial Infarction" *J. of Internal Med.* 225:333–336 (1989).

McDonough et al., "Control of Cardiac $Ca^{2+}$ Levels: Inhibitory Actions of Sphingosine on $Ca^{2+}$ Transients and L–type $Ca^{2+}$ Channel Conductance" *Circul. Res.* 75(6):981–989 (1994).

McGregor, "Selection of Proteins and Peptides from Libraries Displayed on Filamentous Bacteriophage" *Mol. Biotech.* 6:155–162 (1996).

Newby et al., "Biochemical Markers in Suspected Acute Myocardial Infarction: The Need For Early Assessment," *Clin Chem.* 41(9):1263–1265 (1995).

Ohta et al., "A Possible Role of Sphingosine in Induction of Apoptosis by Tumor Necrosis Factor–α in Human Neutrophils" *FEBS Letter* 355:267–270 (1994).

Ohta et al., "Induction of Apoptosis by Sphingosine I Human Leukemic HL–60 Cells: A Possible Endogenous Modulator of Apoptotic DNA Fragmentation Occurring During Phorbol Ester–Induced Differentiation[1]" *Cancer Res.* 55:691–697 (1995).

Olivera et al., "Saphingosine Kinase from Swiss 3T3 Fibroblasts: A Convenient Assay for the Measurement of Intracellular Levels of Free Sphingoid Bases" *Anal. Biochem.* 223:306–312 (1994)

Oral et al., "Sphingosine Mediates the Immediate Negative Inotropic Effects of Tumor Necrosis Factor–α in the Adult Mammalina Cardiac Myocyte" *J. of Biol. Chem.* 272(8):4836–4842 (1997).

Palinski et al., "Cloning of Monoclonal Autoantibodies to Epitopes of Oxidized Lipoproteins from Apolipoprotein E–Deficient Mice" *J. Clin. Invest.* 98(3):800–814 (1996).

Reza et al., "Anti–Idiotypic Monoclonal Antibody Recognizes a Consensus Recognition Site for Phosphatigylserine in Phosphatidylserine–Specific Monoclonal Antibody and Protein Kinase C" *FEBS Letters* 339:229–233 (1994).

Rudenko et al., "Prognosis of trend of post–operation period of congenital heart disease patients," Derwent Publications Abstract XP–002079555 (1993).

Sabbadini et al., "Sphingosine is Endogenous to Cardiac and Skeletal Muscle," *Biochem. and Biophysical Res. Comm.* 193(2):752–758 (1993).

Sabbadini et al., "The Distribution of ATPase Activities in Purified Transverse Tubular Membranes" *Arch. of Biochem. and Biophys.* 223(1):107–119 (1983).

Sabbadini et al., "The Effects of Sphingosine on Sarcoplasmic Reticulum Membrane Calcium Release" *J. of Biol. Chem.* 267(22):15475–15484 (1992).

Sambrook et al., *Molecular Cloning A Laboratory Manual* Cold Harbor Spring Press (1989).

Sergeyev et al., "Lipid Spectrum of the Myocardium of Whit Rats Exposed to Hypoxic Hypoxia" *USSR Report* 15(6):71–74 (1981).

Serres et al., "Temperature and Ph–Sensitive Polymers for Human Calcitonin Delivery" *Pharmaceutical Res.* 13(2):196–201 (1996).

Shapiro, *Chemisty of Sphingolipids* Hermann Paris (1969) (Table of Contents Only).

Shields et al., "The Secretion of Atrial Natriuretic Factor–(99–126) by Cultured Cardiac Myocytes Is Regulated By Glucocorticoids" *J. of Biol. Chem.* 263(25):12619–12628 (1988).

Sung et al., "Production of Lymphotoxin by Isolated Human Tonsillar B Lymphocytes and B Lymphocyte Cell Lines" *J. Clin. Invest.* 84:236–243 (1989).

Umeda et al., "Effective Production of Monoclonal Antibodies Against Phosphatidylserine: Stero–Specific Recognition of Phosphatidylserine By Monoclonal Antibody", *J. of Immunol.* 143:2273–2279 (1989).

Vaddi et al., "Increased Secretion of Tumor Necrosis Factor–$\alpha$ and Interferon–$\lambda$ by Monocuclear Leukocytes in Patients with Ischemic Heart Disease" *Circulation* 90(2):694–699 (1994).

Vemuri et al., "Antisphingolipid Antibodies in the Sera of Leprosy Patients" *Lepr Rev.* 67:95–103 (1996).

Warner et al., "Human Vascular Smooth Muscle Cells" *J of Immunol.* 142(1):100–109 (1989).

Webster et al., "Sphingosine Effects on the Contractile Behavior of Skinned Cardiac Myocytes" *J. Mol. Cell Cardiol.* 26:1273–1290 (1994).

Yatomi et al., "Sphingosine 1–Phosphate, a Bioactive Sphingolipid Abundantly Stored in Platelets, Is a Normal Constituent of Human Plasma and Serum" *J. Biochem.* 121:969–973 (1997).

Zhang et al., "Editorial: Signaling through the Sphingomyelin Pahway" *Endocrinology* 136(10) 4157–4160 (1995).

* cited by examiner

SPHINGOSINE (SPH)

SPHINGOSINE-1-P (S1P)

SPHINGOSYLPHOSPHORYLCHOLINE (SPC)

DIHYDROSPHINGOSINE (DHSPH)

N-STEROYL SPHINGOSINE (CERAMIDE)

KITS FOR EARLY DETECTION OF HEART DISEASE

RELATED APPLICATIONS

This application is a divisional of U.S. patent application Ser. No. 09/084,069, filed May 22, 1998, by Sabbadini et al., and entitled "METHODS FOR EARLY DETECTION OF HEART DISEASE" now U.S. Pat. No. 6,210,976, which in turn claims priority to the U.S. Provisional Patent Application Serial No. 60/049,274, filed Jun. 10, 1997, by Sabbadini, et al., and entitled "DIAGNOSIS OF HEART DISEASES USING SPHINGOLIPIDS," both of which are hereby incorporated by reference herein in their entirety, including any drawings.

FIELD OF THE INVENTION

This invention relates generally to the area of diagnosis of heart disease, and specifically relates to methods of diagnosis of heart failure, cardiac ischemia, or hypoxia by detecting the level, e.g., concentration, of a non-polypeptidic cardiac marker as an indicator of heart damage, particularly chronic underlying coronary artery disease, and for monitoring of therapeutic regimes designed to alleviate cardiac ischemia or hypoxia.

BACKGROUND OF THE INVENTION

Ischemic heart disease is the major form of heart failure. Heart failure affects millions of people worldwide and is the leading cause of death in the United States. The most common manifestation of cardiac ischemia is chest pain (angina pectoris) which can lead to heart attack (acute myocardial infarction or AMI) and sudden death. In addition to those who exhibit clinical symptoms of ischemic heart disease, many other individuals are at high risk of developing heart disease based on indicators such as hypertension conditions, high levels of serum cholesterol and/or family history.

Myocardial ischemic disorders occur when cardiac blood flow is restricted (ischemia) and/or when the oxygen supply to heart muscle is compromised (hypoxia) such that the heart's demand for oxygen is not met. Atherosclerosis of the coronary artery is the most common cause of ischemia-associated symptoms such as angina pectoris. Ischemia and hypoxia can be transient and reversible, but can also lead to infarction. During infarction, cardiac tissue is damaged and the heart cells become permeabilized, releasing a portion of their contents to the surrounding milieu, including cardiac enzymes and other biochemical markers. These cellular markers, such as creatine kinase (CK), lactic acid dehydrogenase (LDH) enzymatic activities and creatine kinase-MB (CKMB) and troponin (I and T) and myoglobin mass levels, are then detectable in the serum.

Current diagnostic procedures generally assess the extent of cardiac tissue damage after clinical signs have appeared. At that point, however, the disease may have progressed to an extent where AMI is imminent or has already occurred. Current methods of identifying and confirming infarction require more time than is often available in emergency situations where rapid evaluation is critical for effective patient treatment and survival. Moreover, about 25% of AMI patients display atypical symptoms and many known tests result in false negatives, resulting in the unintentional discharge of about 5% of patients who have AMI (Mair J. et al., *Clin. Chem.* 41:1266–1272, 1995; Newby L. K. et al., *Clin. Chem.* 41:1263–1265, 1995). In an emergency medical facility, electrocardiography (ECG) monitoring of suspected AMI patients is the most rapid diagnostic method for detecting AMI, although it successfully detects only about half of AMI patients (Mair et al., 1995).

Electrocardiography and currently available diagnostic blood tests are generally not effective for early detection of myocardial ischemia that precedes the damage associated with AMI because the tests detect infarction-associated tissue damage. They are not effective in early detection of chronic underlying coronary artery disease and the resulting myocardial ischemia that precedes the damage associated with AMI. Currently, the only diagnostic for chronic underlying coronary artery disease is ECG monitoring during exercise stress (e.g., treadmill exercise) is generally used to confirm the clinical symptoms of angina. Such stress testing is usually given after the patient has experienced symptoms and sought treatment (e.g., at an emergency medical facility). Although stress testing is sometimes used to screen asymptomatic patients, testing is costly, time-consuming and generally not amenable to routine screening of large numbers of patients. Furthermore, exercise stress test evaluations result in about 15% false negatives.

Diagnostics tests have been developed that use cardiac proteins to determine whether or not the source of the patient's chest pain is cardiac and if so, whether the patient has suffered a myocardial infarct or is suffering from unstable angina (see, e.g., U.S. Pat. Nos. 5,290,678, 5,604,105, and 5,710,008). These tests do not give an early warning for when myocardial infarct is forthcoming. Thus, a non-invasive, sensitive, and reliable point-of-care 'bedside test' is needed for the early detection of cardiac ischemia, particularly for people at risk for heart disease.

In view of the need for rapid and reliable methods for detecting cardiac ischemia in the absence of symptoms, particularly for screening those at high risk of heart disease, the present invention is an early detection assay for cardiac ischemia or hypoxia.

SUMMARY OF THE INVENTION

The present invention provides diagnostic methods for the early detection of heart disease (e.g., heart failure, cardiac ischemia, and cardiac hypoxia) in mammals, particularly humans, by monitoring serum or whole blood levels of non-polypeptidic cardiac markers, e.g., sphingosine and/or its metabolites. For instance, an early event in the course of cardiac ischemia (i.e., lack of blood supply to the heart) is an excess production by the heart. muscle of certain naturally occurring non-polypeptidic compounds, or cardiac markers, such as, but not limited to, sphingosine (SPH; D(+)-erythro-2-amino-4-trans-octadecene-1,3-diol or sphingenine), its isomers, and metabolites; ceramide (Cer, n-acylsphingosine), sphingosine-1-phosphate (S1P), sphingosylphosphorylcholine (SPC, lysosphingomyelin), and glycosphingolipids and lysophospholipids such as lysophosphatidic acid (LPA), and the metabolites of any of the foregoing. The present invention is based on the observation that SPH is increased in the serum and suggests that blood sphingolipid levels represent a new biochemical marker for cardiac ischemia.

Evidence indicates that the cardiac source of tumor necrosis factor alpha (TNFα) may be responsible for the characteristic increased serum sphingolipids resulting from cardiac ischemia. Accordingly, preferred embodiments of the invention provide that serum SPH levels, or levels of other related lipids having a sphingosine backbone, be used in combination with levels of a secondary marker, e.g., serum TNFα, as an index of ischemia. Of course, other non-polypeptidic cardiac markers can also be used in conjunction with a secondary marker such as TNFα to calculate such an index. This dual analyte measure is referred to as Myocardial Risk Factor (MRF).

Kits according to the invention provide cost-effective and rapid tests that can be used to identify and predict, among other cardiac conditions, acute myocardial infarction (AMI) and to confirm that angina pectoris results from cardiac ischemia. In addition, the present invention can be used for simple screenings of early ischemic or hypoxic events before symptoms are presented, e.g., in persons with high risk for heart disease and for persons experiencing other forms of heart failure, including myocarditis, the cardiomyopathies, and congestive and idopathic heart failure. Moreover, the methods and compositions according to the invention can be used to monitor the effectiveness of therapeutic interventions designed to relieve the ischemia and heart failure.

Thus, in one aspect, the invention provides a method of detecting heart disease characterized by cardiac ischeria or hypoxia in a mammal comprising the steps of (a) measuring a level of a non-polypeptidic cardiac marker in the test sample from the mammal; and (b) determining if the level of the cardiac marker measured in the test sample correlates with cardiac ischemia or hypoxia.

"Ischemia" means a condition where the cardiac muscle receives insufficient blood supply, whereas "hypoxia" means a condition where the cardiac muscle receives insufficient oxygen.

The term "mammal" refers to such organisms as mice, rats, rabbits, goats, horse, sheep, cattle, cats, dogs, pigs, more preferably monkeys and apes, and most preferably humans.

In preferred embodiments, the subject of the methods of the invention is a human, and the test sample used is preferably a body fluid. The body fluid is preferably selected from the group consisting of blood, urine, lymph, and saliva, although any other body fluid, such as serum, gastric juices, and bile, may be used. Most preferably the body fluid is blood.

The term "non-polypeptidic cardiac marker" means a compound that is not considered to be a peptide by those skilled in the art, even though it may contain a peptide bond or an amide bond, and is uniquely associated with the heart, such that the heart and cardiac functions are the source of the compound.

The non-polypeptidic cardiac marker is preferably a lipid and more preferably a sphingolipid. A "lipid" means a substance that is insoluble in water that can be extracted from cells by organic solvents of low polarity. Lipids include compounds such as terpenes, steroids, fats, and fatty acids. A "sphingolipid" means a compound that shares the sphingosine backbone containing an 18-carbon chain amino alcohol of the general formula $CH_3(CH_2)_{14}CH(OH)CH(NH_2)CH_2-R$, where R may be any organic substituent. "Sphingosine" means the compound of formula $CH_3(CH_2)_{14}CH(OH)CH(NH_3^+)CH_2OH$, as shown in FIG. 1. The scope of the invention also includes compounds where the carbon chain of the sphingolipid contains centers of unsaturation (i.e., double bonds or triple bonds), or where hydroxide or the amine substituents are further substituted with organic substituents. It is also understood "sphingolipid" refers to any isomer, e.g., threo-sphingosine, erythro-sphingosine, and L and D isomers of a sphingolipid, as well as any metabolite of any of the foregoing non-polypeptidic cardiac markers.

The non-polypeptidic cardiac marker is more preferably sphingosine or one of its metabolites. The metabolite is preferably selected from the group consisting of ceramide (Cer, n-acylsphingosine), sphingosine-1-phosphate (S1P), sphingosylphosphorylcholine (SPC), and dihydrosphingosine (DHSPH). The structures of these metabolites are shown in FIG. 1.

In preferred embodiments, the measuring step of the methods of the invention comprises measuring the marker level by a method selected from the group consisting of chromatography, immunoassay, enzymatic assay, and spectroscopy, where the cardiac marker is directly or indirectly detected. "Marker level" means the amount of the marker in the sample or in the mammal, and refers to units of concentration, mass, moles, volume, preferably concentration, or other measure indicating the amount of marker present in the sample.

The chromatographic method is preferably high performance liquid chromatography (HPLC) or gas chromatography (GC). The spectroscopic method is preferably selected from the group consisting of ultraviolet spectroscopy ((UV or UV/V is spectroscopy), infrared spectroscopy (IR), and nuclear magnetic resonance spectroscopy (NMR).

The immunoassay preferably detects a non-polypeptidic cardiac marker selected from the group consisting of Cer, SPH, S1P, DHSPH, and SPC. Preferably, the immunoassay detects the non-polypeptidic cardiac marker in the test sample using anti-marker antibodies.

The term "antibody" refers to a monoclonal or polyclonal antibody or antibody fragment having specific binding affinity to a non-polypeptidic cardiac marker.

By "specific binding affinity" is meant that the antibody or antibody fragment binds to target compounds with greater affinity than it binds to other compounds under specified conditions. Antibodies or antibody fragments having specific binding affinity to a compound may be used in methods for detecting the presence and/or amount of the compound in a sample by contacting the sample with the antibody or antibody fragment under conditions such that an immunocomplex forms and detecting the presence and/or amount of the compound conjugated to the antibody or antibody fragment.

The term "polyclonal" refers to antibodies that are heterogeneous populations of antibody molecules derived from the sera of animals immunized with an antigen or an antigenic functional derivative thereof. For the production of polyclonal antibodies, various host animals may be immunized by injection with the antigen. Various adjuvants may be used to increase the immunological response, depending on the host species.

"Monoclonal antibodies" are substantially homogenous populations of antibodies to a particular antigen. They may be obtained by any technique which provides for the production of antibody molecules by continuous cell lines in culture. Monoclonal antibodies may be obtained by methods known to those skilled in the art. See, for example, Kohler, et al., Nature 256:495–497, 1975, and U.S. Pat. No. 4,376,110.

The term "antibody fragment" refers to a portion of an antibody, often the hypervariable region and portions of the surrounding heavy and light chains, that displays specific binding affinity for a particular molecule. A hypervariable region is a portion of an antibody that physically binds to the target compound. The term "antibody fragment" also includes single change antibodies.

In preferred embodiments, the determination step of the method of invention is a comparison between the concentration of the cardiac marker and a predetermined value for the marker. In preferred embodiments, the predetermined value is indicative of a normal cardiac condition. This predetermined value can be determined using the methods of the present invention as described in Detailed Description of the Invention, below, and can be specific for a particular patient or generic for a given population. The predetermined value is preferably obtained from a mammal in the same species and approximately the same age as the mammal providing the test sample. In certain embodiments, the predetermined value may have been established by prior measurement of the particular patient's marker levels when the patient was healthy.

In practicing the methods of the invention, the level.(e.g., concentration) of the non-polypeptidic cardiac marker in the test sample is preferably higher than a predetermined value for that marker, which higher level correlates with or indicates ischemia, hypoxia, or another form of heart failure. However, with certain non-polypeptidic cardiac markers, the level of the marker in the test sample may be lower than the predetermined value in order to indicate ischemia, hypoxia, or another form of heart failure.

In a further aspect, the invention relates to a method of detecting heart failure (e.g., cardiac ischemia or hypoxia) in a mammal comprising the steps of (a) measuring a level of one or more non-polypeptidic cardiac markers in a test sample from the mammal; (b) measuring a level of one or more secondary cardiac markers in the test sample; and © determining if the level of the cardiac markers measured in the test sample correlates with cardiac ischemia or hypoxia The secondary cardiac marker(s) is(are) preferably a pro-inflammatory cytokine such as interleukin (IL-1, 2, or 6), interferon gamma (IFNγ), and particularly tumor necrosis factor alpha (TNFα). TNFα has been implicated in the pathophysiology of ischemia and hypoxia. As those in the art will appreciate, the instant methods and compositions may also include measurement of the levels of two (or) more non-polypeptidic cardiac markers, alone or in conjunction with one or more secondary cardiac markers. For purposes of this invention, a "secondary" cardiac marker is an intercellular or intracellular messenger which precipitates or contributes to the underlying cause of heart failure. In other embodiments of this aspect of the invention, the level of one or more "tertiary" cardiac markers can also be determined and used in conjunction with levels determined for the non-polypeptidic cardiac markers(s), or non-polypeptidic and secondary cardiac marker(s) tested. For purposes of this invention, a "tertiary" marker is one associated with disruption of cardiac cells, and generally relates to proteins, polypeptides, and nucleic acids released from ruptured or lyzed cardiac cells. Certain preferred examples of such markers include CK, LDH, CKMB, and troponin. Other preferred examples of such tertiary cardiac markers include nucleic acids specific for cardiac cells, particularly mRNA, expressed predominantly, and preferably only in cardiac cells.

In another aspect, the method of the invention concerns calculating a myocardial risk factor (MRF). As used herein, the MRF has a mathematical relation with the measured level, preferably concentration, of at least one non-polypeptidic cardiac marker and the measured level, preferably concentration, of a second cardiac marker, e.g.,. TNFα. The mathematical relation is preferably a product of the measured level (e.g., concentration) of at least one non-polypeptidic cardiac marker, preferably a sphingolipid, and the measured level (e.g., concentration) of the second marker, preferably TNFα. Of course, other mathematical relationships between different markers are also within the scope of the invention. For example, such relationship may involve two non-polypeptidic cardiac markers, a non-polypeptidic cardiac marker, a secondary cardiac marker, and a tertiary cardiac marker, or a non-polypeptidic cardiac marker and a tertiary marker.

In another aspect, the invention provides for a method of preventing or reducing the severity of a subsequent acute myocardial infarction (or other form of heart failure) by detecting cardiac ischemia or hypoxia, as described herein, and taking a preventive measure. The preventive measure is preferably selected from the group consisting of coronary bypass surgery, preventive angioplasty, and/or administering therapeutically effective amounts of one or more anticoagulants, thrombolytics, or other pharmaceutical products intended to alleviate the ischemic or hypoxic condition.

Furthermore, the methods of the invention allow a health care professional to determine the prognosis of a patient following a cardiac procedure by detecting cardiac ischemia or hypoxia. The cardiac procedure is preferably selected from the group consisting of coronary bypass surgery, preventive angioplasty, and administering one or more anticoagulant, although other cardiac procedures are also within the scope of the present invention.

In another aspect, the invention provides for kits for detecting heart failure, such as may result from cardiac ischemia or hypoxia, in a mammal. Preferably, such kits comprise a composition for detecting an abnormal level of at least one non-polypeptidic cardiac marker in a test sample obtained from a mammal. Preferably, the composition enables measuring the abnormal level in a quantitative manner, although measuring the abnormal level can also be accomplished in a semi-quantitative manner (e.g., is the level above or below a pre-determined threshold value). The composition may preferably comprise a substrate, which may preferably be an antibody which binds to a non-polypeptidic cardiac marker selected from the group consisting of Cer, SPH, S1P, DHSPH, and SPC. The composition may also include one or more other substrates, e.g., an anti-TNFα antibody, to detect other cardiac-specific markers. The substrate may be affixed to a solid support for easy handling. Common forms of solid support include, but are not limited to, plates, tubes, and beads, all of which could be made of glass or another suitable material, e.g., polystyrene, nylon, cellulose acetate, nitrocellulose, and other polymers. The solid support can be in the form of a dipstick, flow-through device, or other suitable configuration.

In a "quantitative" measurement, the step of measuring results in the production of a value which accurately shows the level of the cardiac marker in the test sample. In a "semi-quantitative" measurement, the step of measuring results in the indication of whether the level of the cardiac marker is within a particular range. Semi-quantitative methods include, for example, but are not limited to, color indicators or depiction of certain symbols, where each color or symbol represents a concentration range.

Preferably, the level of the cardiac marker(s) detected in the practice of this invention is(are) different than a standard or reference measure that indicates a normal cardiac condition. More preferably, the level of the cardiac marker detected is greater than the standard measure.

In preferred embodiments, the level of the cardiac marker (s) measured in accordance with the invention are detected using. a "non-invasive" method, i.e., one which does not require piercing the skin of the subject mammal to obtain the test sample. Non-invasive methods include, but are not limited to, testing body fluids such as saliva, urine, and sweat, or using imaging techniques.

Preferably, the level of the cardiac marker is measured using a kit of the invention by a method selected from the group consisting of chromatography, immunoassay, enzymatic assay, and spectroscopy, where the marker is directly or indirectly detected. The chromatographic method is preferably high performance liquid chromatography (HPLC) or gas chromatography (GC). The spectroscopic method is preferably selected from the group consisting of ultraviolet spectroscopy, infrared spectroscopy, and nuclear magnetic resonance spectroscopy. With regard to the non-polypeptidic cardiac marker, the immunoassay preferably detects Cer, SPH, S1P, DHSPH, or SPC.

In another aspect, the invention provides devices for detecting cardiac ischemia or hypoxia in a mammal, where the device informs the user of an abnormal level of at least one non-polypeptidic cardiac marker in a test sample obtained from a mammal.

The informing step preferably includes the step of detecting said cardiac marker, which, in turn, is preferably performed by a non-invasive procedure. The informing step also preferably comprises the step of comparing the level of the marker with a predetermined value. Finally, the informing step preferably includes a step of alerting a user, who may or may not be the wearer of the device, as to the level of the marker. The device may display the level of the marker, sound an alarm when the level of the maker surpasses a pre-determined threshold, or inform emergency personnel, such as police, ambulance, or fire department.

The mammal for whom the device is used is preferably a human. The device preferably tests a body fluid for the presence of a non-polypeptidic cardiac marker, which preferably is a sphingolipid, for example, sphingosine or a metabolite thereof. The sphingosine metabolite is preferably selected from the group consisting of Cer, S1P, SPC, and DHSPH.

Yet another aspect of the invention concerns compositions for detecting an abnormal level (e.g., concentration) of at least one non-polypeptidic cardiac marker in a test sample (preferably a body fluid) obtained from a mammal, particularly a human. In certain embodiments, the level of the non-polypeptidic marker is measured quantitatively; in other embodiments, the measurement is semi-quantitative.

In preferred embodiments of this aspect, the composition comprises an antibody, anti-body fragment, or antigen binding domain of an antibody, that specifically binds a non-polypeptidic cardiac marker. In embodiments employing an antibody, the antibody can be a polyclonal, and preferably a monoclonal antibody. In certain embodiments, the non-polypeptidic cardiac marker detected by the composition is a lipid, preferably a sphingolipid or a metabolite thereof, particularly Cer, SPH, S1P DHSPH, and SPC.

Compositions according to the invention may also comprise, in addition to a moiety capable of detecting a non-polypeptidic cardiac marker, a second moiety capable of detecting a secondary cardiac marker (e.g., TNFα, IL-1, IL-2, IL-6, and IFNγ), and/or a third moiety capable of detecting a tertiary cardiac marker (e.g., CK, CKMB, LPH, a troponin, and a nucleic acid, particularly a nucleic acid specific to cardiac cells). When the tertiary cardiac marker comprises a nucleic acid probe substantially complementary to at least a sufficient portion of the nucleotide sequence of the nucleic acid so as to enable selective hybridization between the probe and nucleic acid stringent conditions.

In preferred embodiments, the compositions of the invention further comprise a solid support to which the moiety detecting the cardiac marker(s) is or can be attached. In certain embodiments, attachment of the detecting moiety, e.g. an antibody or nucleic acid probe, is via a covalent linkage with the solid support. In other embodiments, attachment may be via a non-covalent linkage, for example, between members of a high affinity binding pair. Many examples of high affinity binding pairs are known in the art, and include biotin/avidin, ligand/receptor, and antigen/antibody pairs.

The summary of the invention described above is non-limiting and other features and advantages of the invention will be apparent from the following detailed description, and from the claims.

DETAILED DESCRIPTION OF THE INVENTION

The present invention concerns methods and compositions for early diagnosis of ischemic heart disease or other forms of heart failure by detecting levels non-polypeptidic cardiac markers, such as sphingosine (SPH) and/or its metabolites, alone or in conjunction with one or more other cardiac markers in a test sample from a mammal. The invention is based on the inventor's discovery that an early event in the course of heart failure, for example, that caused by cardiac ischemia, is excess production by the heart muscle of certain non-polypeptidic cardiac markers, including certain lipids, among which are SPH and its metabolites, Cer, S1P, DHSPH, and SPC.

I. The Role of SPH in Myocardial Infarction

Figure 1:
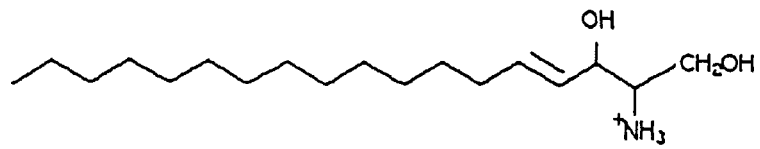
FIG. 1 shows the chemical structure of sphingosine (SPH; D(+)-erythro-2-amino-4-trans-octadecene-1,3-diol or sphingenine), sphingosine-1-phosphate (S1P), sphingosylphosphorylcholine (SPC; lyso-sphingomyelin), ceramide (Cer, an n-acyl sphingosine) and dihydrosphingosine (DHSPH; sphinganine). All of these lipids share the sphingosine backbone containing a long-chain 18-C amino alcohol. Other sphingolipids include N,N-dimethyl-sphingosine, sphingomyelin (n-acylsphingosine-1-phosphocholine) and various glycosphingolipids (cerebrosides and gangliosides). Erythro, threo, D, L, and other sphingolipid isomers are also included within the scope of this invention.
Figure 1:
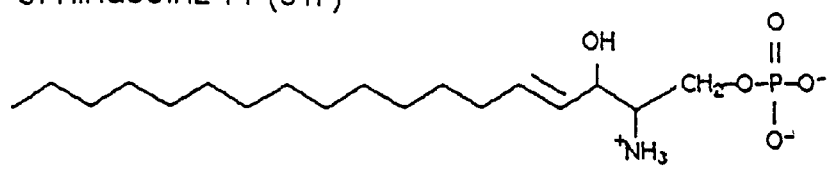
Figure 1:
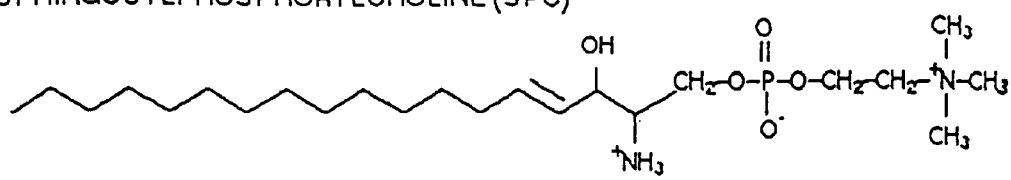
Figure 1:
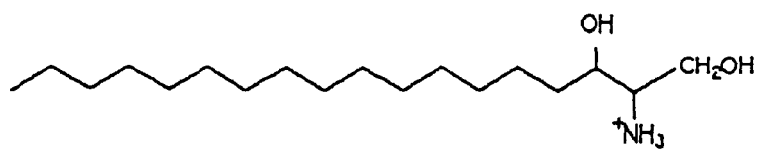
Figure 1:
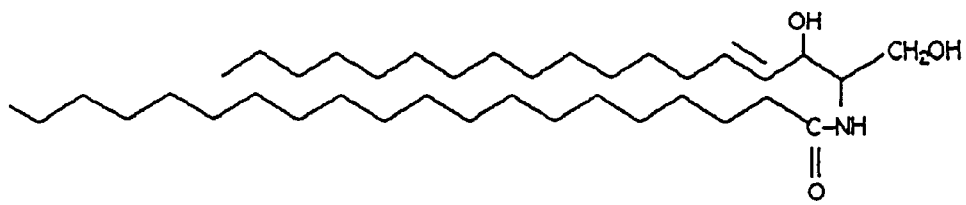

The chemical structures of Cer, SPH, S1P, and SPC are shown in FIG. 1. These sphingolipids all share the same chemical backbone of $CH_3(CH_2)_{12}CH=CHC(OH)CH(NH_2)CH_2$— to which is attached either a hydroxyl, phosphate or phosphorylcholine moiety. As shown in FIG. 1, the amino group of the backbone can be positively charged or substituted. Although not shown in FIG. 1, dihydrosphingosine (or sphinganine) is another metabolite of SPH known in the art (C. A. Grob, *Record Chem. Progr.* (*Kresge-Hooker Sci. Lib.*) 18:55–66, 1957; D. Shapiro, *Chemistry of Sphingolipids* (Hermann, Paris, 1969)). A variety of methods of detecting these molecules in body fluids, e.g., blood or serum, can be used to detect actual or impending heart failure, such as that associated with myocardial ischemic and hypoxic conditions. Based on results presented herein, levels of SPH and/or its metabolites in body fluids provide an early biochemical marker for cardiac ischemia or hypoxia Sphingolipids (e.g., SPH, S1P, DHSPH, or SPC) can be extracted from the serum of patients with ischemic heart disease or controls without cardiac ischemic conditions and derivatized with a fluorescent marker (e.g.; o-pthalaldehyde, OPA) for chromatographic detection. Such derivatized sphingolipids can then be detected and quantified by a variety of methodologies, including HPLC.

Although not wishing to be bound to a particular theory, data suggests that inflammatory cytokines, particularly TNFα, induce increased production of SPH and its metabolites, either directly or indirectly. For example, it is believed that TNFα produces cardiac acidosis leading to increased SMase activity and increased SPH production. The SPH then acts on cardiac calcium channels, resulting in uncontrolled calcium release. The combined actions of TNFα and SPH also promote apoptosis, leading to increased release of intracellular SPH and its metabolites into the serum, and further leading to myocardial infarct. The inventor has published data indicating that TNFα activates SPH production (Krown et al., *J. Clin. Invest.* 98:2854–2865, 1996), and that the resulting SPH and its metabolites has adverse effects on cardiac calcium channels (McDonough et al., *Circ. Res.* 75:981–989, 1994; Dettbarn et al., *J. Mol. Cell. Cardiol.*, 26:229–242, 1994; Krown et al., *FEBS Letters* 376:24–30, 1995; Sabbadini et al., *J. Biol. Chem.* 267:15475–15484, 1992; Webster et al., *J. Mol. Cell. Cardio.* 26:1273–1290, 1994) and cardiac cell death (Krown et al., *J. Clin. Invest.* 98:2854–2865, 1996).

Such cardiac hypoxia and ischemia result in a cycle whereby the acidic conditions of the ischemic heart stimulate excess SPH production which, in turn, inhibits the cell's ability to extrude protons. Increased intracellular acidic conditions further stimulate SPH production in a positive feedback manner to further increase intracellular levels of both protons and SPH. The inventor believes that decreased intracellular pH has profound adverse effects on the cell's contractile machinery, and that increased SPH levels cause the uncontrolled release of calcium from the sarcoplasmic reticulum membranes and the L-type calcium channel, thus preventing the cell from regulating its beat-to-beat contractile behavior. Sphingolipid-mediated acidosis and calcium deregulation activates apoptosis, leading to cell death and subsequent impaired cardiac function. SPH and its metabolites are useful as early indicators of heart failure because these compounds appear early in conditions such as cardiac ischemia and hypoxia, before biochemical compounds associated with cardiac cell death are released.

This invention is based in part on the discovery that in ischemic patients, the levels of serum sphingolipids are significantly higher than those detected in non-ischemic controls. Based on the results obtained, levels of SPH that are diagnostic of heart failure associated with cardiac ischemia or hypoxia are generally greater than 100 pmol/mL. SPH levels diagnostic of cardiac ischemia or hypoxia are preferably in a range of about 200 pmol/mL to about 2,500 pmol/mL, more preferably in a range of about 300 pmol/mL to about 2,000 pmol/mL, and most preferably in a range of about 400 pmol/mL to about 1,500 pmol/mL.

For the metabolites of SPH, high serum (or other body fluid) levels are similarly diagnostic of cardiac ischemia or hypoxia. For serum S1P, diagnostic levels are generally greater than 100 pmol/mL. In serum, S1P levels diagnostic of cardiac ischemia or hypoxia are preferably in a range of about 200 pmol/mL to about 2,500 pmol/mL, more preferably in a range of about 300 pmol/mL to about 2,000 pmol/mL, and most preferably in a range of about 400 pmol/mL to about 1,500 pmol/mL. For SPC, diagnostic levels in serum are generally greater than 100 pmol/mL. SPC levels diagnostic of cardiac ischemia or hypoxia are preferably in a range of about 200 pmol/mL to about 2,500 pmol/mL, more preferably in a range of about 300 pmol/mL to about 2,000 pmol/mL, and most preferably in a range of about 400 pmol/mL to about 1,500 pmol/mL. Similar serum levels of DHSPH are diagnostic of cardiac ischemia.

Although HPLC can be used to detect and quantify cardiac markers, including non-polypeptidic cardiac markers such as SPH in body fluids such as serum, other methods of detecting such markers are also acceptable. For example, enzymatic assays can be used to indirectly detect sphingolipids (or other non-polypeptidic cardiac markers) in test samples. Such assays include, for example, purification of sphingosine kinase from cultured cells which is used in a coupled assay employing pyruvate kinase and its substrate phosphoenblpyruvate to detect hydrolysis. The product of the coupled reaction is pyruvic acid, and the drop in pH resulting from this product is then detected by a variety of known methods such as detecting pH-dependent polymer breakdown that results in a measurable change in impedance. Similarly, sphingosine kinase in blood or serum can be detected in a coupled assay employing luciferase to detect ATP hydrolysis. Such assays are suitable for indirectly detecting blood levels of SPH but not S1P or SPC.

Immunodiagnostic assays, using a variety of known methods, can also be used to detect cardiac markers, including non-polypeptidic cardiac markers such as sphingolipids and their metabolites, in body fluids, including blood or serum. Antibodies and antibody fragments specific for Cer, SPH, DHSPH, S1P, and SPC and other such markers can be produced and used to quantitatively or semi-quantitatively detect the presence of one or more of such markers in whole blood, serum, or other body fluids using standard immunoassays. Similarly, immunoassays that detect the presence of anti-sphingolipid (or other non-polypeptidic cardiac markers) antibodies in body fluids can be used to indirectly test for increased levels of such marker(s) in patients with chronic conditions associated with heart failure, including chronic ischemia and hypoxia. This assay is based on the assumption that patients experiencing such chronic conditions produce antibodies to these markers as a consequence of their elevated blood levels by analogy to the anti-lactosylsphingosine antibodies observed in patients with colorectal cancer (Jozwiak W. & J. Koscielak, *Eur. J. Cancer Clin. Oncol.* 18:617–621, 1982) and the anti-galactocerebroside antibodies detected in the sera of leprosy patients (Vemuri N. et al., *Leprosy Rev.* 67:95–103, 1996).

Detection of one or more secondary markers such as TNFα can be combined with detection of one or more non-polypeptidic cardiac marker(s), such as SPH and/or its metabolites, as an early indicator of heart failure, such as may be caused by cardiac ischemia or hypoxia Because production of secondary cardiac markers such as TNFα is also associated with heart failure (such as may be caused by cardiac ischemia) and may induce increased levels of non-polypeptidic cardiac markers such as SPH and its metabolites in body fluids (e.g., blood and serum), the diagnostic combination of the level of one or more secondary markers such as TNFα and levels of a non-polypeptidic cardiac marker such as a sphingolipid serve as a more sensitive indicator of heart failure. Accordingly, the product of the levels of the non-polypeptidic cardiac marker and the secondary marker(s) can be used to provide a quantitative measure of risk of ischemia or hypoxia referred to as the "Myocardial Risk Factor" (MRF).

Detection of non-polypeptidic cardiac markers, such as sphingolipids (including SPH and/or its metabolites) at levels characteristic of ischemia, hypoxia, or other conditions causally related to heart failure, preferably using a test kit, is useful for identifying these conditions in angina patients or individuals at risk for ischemic heart disease. The assay is also useful for diagnosis of AMI and other forms of heart failure. The present invention is useful for simple screening of persons at risk for heart disease for ischemic or hypoxic conditions before traditional symptoms are detected. The invention is also useful for following the progress of therapeutic regimes intended to treat myocardial ischemia, and thus will have important prognostic value. Methods and compositions of the invention can also be used for preventing the onset of AMI by allowing the patient or a health care professional to use the methods of the invention to detect the conditions that would result in AMI and taking preventive measures, such as angioplasty.

II. Sphingosine Produced by the Cardiac Cells of Experimental Animals has Pathophysiological Effects Resembling Heart Failure Sphingosine (SPH; D(+)-erythro-2-amino-4-transoctadecene-1,3-diol or sphingenine) is a lipid second messenger that the inventor has found to be endogenous to cardiac muscle tissue (Dettbarn et al., *J. Mol. Cell. Biol.* 26:229–242, 1994; Sabbadini et al., *Biochem. Biophys. Res. Comm.* 193:752–758, 1993). Work published by the inventor suggests that SPH has dramatic effects on the ability of the muscle cells to regulate calcium (Dettbarn et al., 1994; Krown et al., *FEBS Letters* 376:24–30, 1995; Sabbadini et al., *J. Biol. Chem.* 267:15475–15484, 1992; Webster et al., *J. Mol. Cell. Cardio.* 26:1273–1290, 1994). Low levels of SPH block calcium movement whereas very high levels have the opposite effect of initiating uncontrolled calcium release and overload (Sabbadini et al., 1992). The acute actions of SPH are specific and the sites of action in the heart are the sarcoplasmic reticulum calcium release channel (Dettbarn et al., 1994; Sabbadini et al., 1992) and the L-type calcium channel of the surface membranes (Krown et al., 1995; McDonough et al., *Circ. Res.* 75:981–989, 1994). The sphingosine derivative, ceramide, has similar actions. Cardiac cell contractility is consequently impaired (Kramer et al., *Circ. Res.* 68:269–279, 1991; Webster et al., 1994). Thus, SPH is a negative inotropic agent and acts as a calcium channel agonist. The calcium deregulation, negative inotropy, and eventual calcium overload produced by SPH in experimental animal models resembles the pathophysiological changes that the heart experiences during ischemia or other forms of heart failure.

The inventor has demonstrated that chronic treatment of neonatal and adult cardiac cells in culture with physiologically relevant levels of SPH and its immediate metabolite, S1P, results in the activation of cardiomyocyte cell death by apoptosis (Krown et al., *J. Clin. Invest.* 98:2854–2865, 1996). Apoptosis is a form of programmed cell death, and determines the size of myocardial infarcts (Kajstura et al., *Lab. Invest.* 74:86–107, 1996). Sphingosine production has been implicated as an early signaling event in apoptotic cell death in a variety of cell types (Cuvlilier et al., *Nature* 381:800–803, 1996; Ohta et al., *Cancer Res.* 55:691–697, 1995; Ohta et al., *FEBS Letters* 355:267–270, 1994). Activation of the sphing myelin signal transduction cascade is a key early event in the cytotoxic (apoptotic) effects of TNFα (Zhang and Kolesnick, *Endo.* 136(10):4157–4160, 1995), and the inventor has shown that TNFα can cause significant apoptosis in cultured rat cardiomyocytes apoptosis (Krown et al., *J. Clin. Invest.* 98:2854–2865, 1996).

Activity of the enzyme sphingomyelinase (SMase), an enzyme likely activated by TNFα in heart tissue (Oral et al., *J. Biol. Chem.* 272:4836–4842, 1997), is increased in the acidotic hearts of experimental animals (Franson et al., *Am. J. Physiol.* 251(5 pt 2):H1017-H1023, 1986). SMase is the principle enzyme responsible for SPH production in cells and the inventor has localized this enzyme to muscle tissue (Sabbadini et al., 1992). There is also evidence from animal models of ischemia that the levels of the immediate precursor of SPH, ceramide, are increased in ischernic brain tissue and that ceramide levels are a consequence of increased sphingomyelin breakdown (Kubota et al., *Japan J. Exp. Med.* 59:59–64, 1989).

Other supporting data indicate that sphingomyelin levels, the precursor of ceramide and sphingosine, increase in hypoxic experimental animals (Sergeev and Gribanov, *Kosm. Biol. Aviakosm. Med.* 15:71–74, 1981), although others have found that sphingomyelin levels decrease in the cerebral cortex of ischemic rats commensurate with increased levels of ceramide (Kubota et al., 1996). While not wishing to be bound by a particular theory, these data support the understanding that the conditions created during hypoxia and ischemia cause the activation of SMase and the subsequent abnormal elevation of cardiac cell SPH levels. The lysosomal isoform of SMase (acidic or aSMase) could be activated by the acidic conditions of hypoxia and could complement activation of the plasma membrane isoform of SMase (neutral or nSMase). The nSMase of cardiomyocytes is likely activated by TNFα. TNFα is released from ischemic cardiac tissue and the TNFα-induced SPH production is an early event in cardiac ischemia.

This invention is in part based on the belief that an early event in cardiac ischemia is TNFα-induced sphingolipid production followed by sphingolipid-dependent acidosis that results in additional sphingolipid synthesis by the acidic form of aSMase, whose source is the lysosome. Sphingosine is a well-known inhibitor of protein kinase C and the system of Na/H exchange which is activated by the kinase to extrude unwanted acid (Lowe et al., *J. Biol. Chem.* 265:7188–7194, 1990). As disclosed in Section I, above, cardiac hypoxia, ischemia, and other conditions which cause heart failure can create a cycle whereby the acidic conditions of the ischemic, hypoxic, or otherwise failing heart stimulate excess sphingolipid production, leading to uncontrolled release of calcium from the sarcoplasmic reticulum membranes and the L-type calcium channel, thus preventing the cell from regulating its beat-to-beat contractile behavior.

Deregulated heart calcium levels can also exacerbate the situation by promoting Na/Ca exchange and indirectly acidifying the cell by stimulation of the Na/H exchanger (Gottlieb et al., *Proc. Natl. Acad. Sci., USA* 92:5965–68, 1995). Sphingolipid-mediated acidosis and subsequent calcium deregulation activate the cell death program and result in apoptosis. In the end, cardiac function suffers from the loss of cells by apoptosis as well as the negative inotropic effects of SPH and pH on surviving cardiomyocytes.

Cell culture studies performed in the inventor's laboratory have demonstrated that cardiomyocytes can "secrete" SPH into the (cell-conditioned) culture medium (SPH 700 pmol/mL). These observations show that SPH and its metabolites could be leaked into the blood from cardiac cells experiencing the hypoxia and acidosis brought about by ischemia. Yatomi et al. reported that S1P is present in human plasma and serum (Yatomi et al., *J. Biochem.* 121:969–973, 1997). No other sphingolipids, including SPH, were measured, and these workers speculated that S1P was released from platelets during clotting. Plasma was incubated with 3H-sphingosine for as long as 2 hours to determine if S1P could be formed from any component of plasma. The SPH was stable for 2 hours in plasma and only platelet-rich plasma converted SPH to S1P, suggesting that the platelets were the source of S1P. Significantly, the source of SPH for S1P formation by platelets was not discussed, nor was a potential role of SPH and/or S1P in cardiac ischemia. In contrast, and while not wishing to be boundby a particular theory, the present invention is based on the understanding that the SPH released from cardiac cells during the early stages of cardiac ischemia leaks is "secreted" or otherwise escapes into the blood from cells damaged by the hypoxic or ischemic conditions, and is acted upon by sphingosine kinase present in blood platelets. The S1P released from the platelets then stimulates thrombus formation. Thus, the SPH released from cardiac cells damaged by hypoxic or ischemic conditions eventually results in the production of a myocardial infarction.

III. Tumor Necrosis Factor Alpha (TNFα)

At the molecular level, pro-inflammatory cytokines such as tumor necrosis factor alpha (TNFα) have been implicated in the pathophysiology of ischemia and hypoxia. Elevated serum TNFα levels occur during hypoxic conditions associated with cardiac ischemia and reperfusion injury, and circulating TNFα levels are markedly increased after acute myocardial infarction (Herskowitz A. et al., *Am. J. Pathol.* 146–419428, 1995;.Vaddi K. et al., *Circ.* 90:694–699, 1994; Lefer A. M. et al., *Science* 24:61–63, 1990; Maury C. P. J. & A.-M. Teppo. *J. Intern. Med.* 225:333–336, 1989). Reduction in serum TNFα levels is associated with improvements in ischemic conditions (Hennein H. A. et al., *Circ.* 88(4):I-247, 1993). In human patients suffering from chronic heart disease, high crum levels of TNFα are detectable and increased TNFα levels occur immediately after coronary bypass surgery (Levine et al., *New Eng. J. Med.* 323:236–241, 1990; Deng M. C. et al., *Eur. J. Cardiol.* 9:22–29, 1995; Hennein H. A. et al., *J. Thorac. Cardiovasc. Surg.* 108:626–35, 1994).

Pro-inflammatory cytokines, such as TNFα, interleukines 1, 2, and 6 (IL-1, IL-2, and IL-6), are generally produced by myeloid-derived cells such as macrophages, neutrophils and lymphocytes (Kelker H. et al., *Int. J. Cancer* 36(1):69–73, 1985; Cuturi M. et al., *J. Exp. Med.* 165:1581–1594, 1987; Sung S. et al., *J. Clin. Invest.* 84(1):236–243, 1989; Liebermann A. et al., *Proc. Natl. Acad. Sci. USA* 86:6348–6352, 1989; Lindemanm A. et al., *J. Clin. Invest.* 83(4):1308–1312, 1989). Smooth muscle and endothelial cells have been suggested as a source of TNFα (Warner, S., and P. Libby, *J. Immunol.* 142:100–109, 1989; Libby, P., et al., *Am. J. Pathol.* 124:179–185, 1986). It has also been postulated that the heart is a source of TNFα (Giroir B. et al., *J. Clin. Invest.* 90:693–698, 1992; Giroir P. B. et al., *Am. J. Physiol.* 267:H118-H124, 1994; Gurevitch J. et al., *J. Am. Coll. Cardiol.* 28(1):247–252, 1996). Ischemic rat hearts perfused in a Langendorff apparatus have been reported to secrete TNFα into the effluent during the first minute of reperfusion (Gurevitch et al., 1996).

IV. Heart Cells are the Source of Serum TNFα and SPH

Data collected in connection with the experiments which gave rise to this invention demonstrate that both neonatal and adult rat cardiomyocytes in culture, devoid of fibroblasts and endothelial cells, are capable of secreting large amounts of TNFα in response to the bacterial endotoxin, lipopolysaccharide (LPS), which is a well-know secretagogue for the cytokine. The amount of secreted TNFα can reach 1500 pg/mL, which is within the range of TNFα that is capable of producing significant apoptotic cell death in cardiomyocytes (Krown et al., 1996). Further supporting the contention that heart cells are a significant source of TNFα is data showing that TNFα levels in the pulmonary arteries of human subjects undergoing balloon angioplasty is greater than the serun levels of TNFα found in the femoral veins of the same patients, which data suggests that, during ischemia (induced by balloon inflation), the ischemic heart tissues produce TNFα which then is released into the general circulation from the coronary sinuses and the pulmonary artery. The TNFα in the pulmonary artery of coronary angioplasty patients correlates well with changes in pulmonary artery SPH levels. Based on these data, it is believed that the cardiac source of TNFα is a major stimulus for cardiac cell SPH production.

In sum, the above data indicate that the elevated serum SPH and TNFα seen in various forms of myocardial ischemia, such as occurs during coronary angioplasty, results from SPH and TNFα released into the circulation by ischemic heart cells.

V. Neither SPH Nor TNFα are Elevated in the Serum as a Result of Skeletal Muscle Ischemia Since it has previously been demonstrated that SPH is present as a signaling molecule in skeletal muscle (Sabbadini et al., 1993), it was important to determine if skeletal muscle could be the source of serum SPH. Skeletal muscle mass represents 30–40% of total body weight and could represent a very large source of serum SPH. To confirm that the source of serum SPH is specifically associated with cardiac ischemia and not skeletal muscle, several Olympic athletes and Navy subjects were tested for serum SPH before and after inducing severe skeletal muscle ischemia. Skeletal muscle ischemia was induced by asking the subjects to exercise to exhaustion on treadmills placed in a 49° C. room, and was confirmed by measuring serum lactate. Prior to the exercise regime, serum SPH averaged 5.18±4.5 pmol/rL (n=4) and slightly decreased to a level of 4.02±3 pmol/mL after exhaustive exercise. Moreover, these serum SPH values were substantially lower than those observed in the ischemic patients described above. Importantly, serum TNFα levels were not increased in these subjects undergoing severe skeletal muscle ischemia. For example, serum TNFα values for the military personnel were 1.22±0.49 pg/mL before exercise and rose insignificantly to 1.39±0.23 gimL after exercise for 20 min. at 49° C. (120° F.) ambient temperature.

VI. Determination of the Predetermined Marker Value

In certain embodiments of the present invention, the level of the non-polypeptidic and/or secondary cardiac marker(s) or the MRF calculated for a test sample is compared with a predetermined value for that marker in order to determine if evidence of heart failure, such as may be induced by cardiac ischemia or hypoxia, exists. The predetermined value for one or more of such markers can be established by one of at least two ways. For example, it can be established by gathering data from the mammal (e.g., a human) at risk of AMI prior to the onset of signs for heart disease, or by testing other healthy mammals in preferably the same species and age group as the patient.

In the first method, the physician treating the patient may determine that the patient, based on statistical, genetic, familial, or other factors generally known in the art of medicine, is at risk of an AMI. The physician can then determine the level of one or more non-polypeptidic cardiac markers or the MRF for the patient to establish a baseline. Alternatively, or in addition, the physician may also determine the level of one or more secondary markers (e.g., TNFα, IL-1, 2, 6, or another cytokine) to establish a baseline. The methods of the invention provide for the comparison of the level of the non-polypeptidic cardiac marker(s) and/or secondary marker(s) in the patient with this baseline in order to detect impending heart failure, such as may be caused by cardiac hypoxia or ischemia.

In the second method, the physician or other health care professional, including a medical statistician, can determine the level of the cardiac marker(s) or the MRF in individuals determined to be healthy by a physician. The levels of the individuals in the same age group can be grouped together and their average and standard deviation determined. This value will represent the predetermined value to which the level of the cardiac marker in the patient will be compared in order to detect cardiac hypoxia or ischemia.

VII. Early Detection can Lead to Prevention of Acute Myocardial Infarction

The methods and compositions of the present invention allow for early detection of cardiac ischemia or hypoxia, i.e., conditions that lead to AMI and other forms of heart failure. Using the instant methods, once ischemia or hypoxia has been detected, the patient can present himself or herself to an emergency medical facility, where measures can be taken in order to prevent heart failure from occurring. These measures include, but are not limited to, angioplasty, coronary bypass surgery, or administration of one or more anticoagulant or thrombolytic drugs.

The purpose of such preventive measures is to alleviate the ischemic or hypoxic conditions prior to the onset of AMI or other types of heart failure. In contrast, today the above measures are used after an AMI has occurred, or while the patient is experiencing heart failure. The present invention, however, allows for early detection of conditions which cause heart failure, prior to the onset of the symptoms and the tissue damage associated therewith.

VIII. Determining Prognosis Following a Cardiac Procedure

The methods and compositions of the present invention allow physicians and other health care professionals to determine the success of a cardiac procedure immediately following the procedure. For instance, following angioplasty or stent placement in a cardiac artery, the level of one or more cardiac marker(s) or the MRF can be monitored as described herein to determine whether the ischemic or hypoxic conditions are being alleviated. Thus, the success of the operation can be immediately determined. If the procedure did not result in the desired results, as determined by the level of the cardiac marker(s) or the MRF measured, then further procedures can be employed prior to the patient suffering an complete or partial heart failure.

EXAMPLES

The examples below are non-limiting and are merely representative of various aspects and features of the present invention.

General Procedures

Unless defined otherwise, all scientific and technical terms used herein have the same meaning as commonly understood by those skilled in the art. Unless mentioned otherwise, the techniques employed or contemplated herein are standard methodologies well known to those of ordinary skill in the art. The following chemicals, assays and procedures were used to obtain the results presented herein. Those skilled in the art will appreciate that other sources of reagents and well known methods could be substituted without departing from the scope of the invention.

Chemicals

Chemicals were obtained as follows: D-Sphingosine [D(+)-erythro-2-amino-4-trans-octadecene-1,3-diol] from Matreya, Inc. (Pleasant Gap, Pa.); sphingosine-1-phosphate from Biomol (Plymouth Meeting, Pa.); o-Pthalaldehyde from ICN Biochemicals (Cleveland, Ohio) and HPLC grade methanol from Fisher Scientific (Tustin, Calif.). Other chemicals, including sphingosylphosphorylcholine and DL-erythro-dihydrosphingosine, were obtained from Sigma Chemical Co. (St. Louis, Mo.).

Stock solutions of sphingosine and other sphingolipids were prepared as complexes with fatty acid-free bovine serum albumin (BSA) to provide solutions of the compounds that are essentially free of micelles or organic solvents.

Sphingolipid Extraction and Chromatographic Detection Methods

Sphingosine levels were determined by HPLC performed essentially as described previously (Sabbadini, et al., 1993). Briefly, fresh tissue was excised from the animal and homogenized at 5° C. in the presence of four volumes of 50 mM potassium phosphate buffer, pH 7.0. Similarly, SPH can be extracted from whole blood or serum samples. Samples (300 μL) of the crude homogenates, blood or serum were added to 750 μL of a chloroform:methanol solution (1:2) and vortexed several times. Chloroform (about 500 μL) was then added, followed by 500 μL of 1 M NaCl. The extract was centrifuged briefly to promote phase separation and the upper aqueous phase was removed by aspiration. Then, 500 μL of 1 M NaCl was added, and the centrifugation and aspiration steps were repeated. Residual chloroform was removed by vacuum drying for 30 min. in a vacuum centrifuge (SpeedVac, Savant Instruments, Inc., Farmingdale, N.Y.). The residue was suspended in 750 μL of 0.1 M KOH in chloroform:methanol (1:2). The suspension was bath-sonicated and incubated at 37° C. for 1 hr. When the extract had cooled to room temperature, 500 μL of chloroform and 500 μL of 1 M NaCl were added, the sample was mixed, centrifuged and the upper phase removed by aspiration. The NaCl extraction step was repeated twice and the organic phase was vacuum dried with centrifugation for 30 min. The extracts were derivatized for 10 min. with 50 μL of a solution of 0.5 mg/mL o-pthalaldehyde (OPA), 3% boric acid, pH 10.5, and 0.05% β-mercaptoethanol. Then, 50 μL of methanol and 350 μL of HPLC running buffer (5 mM phosphate, pH 7.0, in 90% methanol) were added to each sample and the OPA-derivatized samples were analyzed by HPLC using standard methods on a Waters HPLC Maxima 820 Chromatography Workstation (Millipore Corp., Ventura, Calif.), including a Waters 470 scanning fluorescence detector. Fluorescence was detected at an excitation wavelength of 340 nm and an emission wavelength of 455 nm.

The sphingolipids were separated by reverse-phase chromatography on a 250 H 7 mm C18, 300 Angstrom pore Brownlee column (Applied Biosystems, Foster City, Calif.) fitted with an Aquapor C18 guard column. Samples were run isocratically at 1.25 mL/min using the running buffer, resulting in an efficiency of extraction of about 50% based on the recovery of SPH standards. The retention times for the standards were: about 15 min for SPH; about 5 min for S1P, and about 20 min for SPC.

Example 1

Serum SPH Levels in Human Patients Experiencing Cardiac Ischemia

Serum samples were taken from patients presenting themselves to an emergency medical facility, under a strict human subject protocols. Three patient groups were examined for serum levels of both SPH and TNFα: (1) patients suspected of AMI and subjected to exercise stress testing; (2) patients undergoing coronary angioplasty; and (3) patients in the early phases of acute myocardial infarction.

Serum from three control groups not exhibiting any clinical symptoms of myocardial ischemic disorders was also tested. These control groups were: (1) age-matched subjects (47 to 79 yrs old) enrolled in an adult fitness program; (2) healthy military personnel at rest and exercising to exhaustion on treadmills at 49° C. (120° F.) ambient temperature; and (3) athletes at an Olympic Training Center at rest and exercising to exhaustion on treadmills at 49° C. ambient temperature.

Patients with confirmed myocardial ischemia had significantly higher SPH levels than any of the control groups. Serum SPH levels for the military personnel and Olympic athletes were combined as one control group (n=6) with resulting serum SPH levels of 4.18±1.8 pmoL/mL. Serum SPH for the age-matched control group (n=15) averaged 99.3±32.4 pmol/mL. When the three ischemic patient groups were combined as one group, an average serum SPH level of 697±0.7 pmol/mL was obtained. This value was about 7-fold higher than the age-matched control group and about 160-fold higher than well-conditioned military personnel and athletes undergoing severe exercise stress.

For comparison with the SPH levels detected, the levels of biochemical markers known to be associated with cardiac tissue damage were also determined. For sixteen of the eighteen ischemic patients, the increased SPH levels detected were consistent with high levels of CK (in the range of 17–810 U/mL) and high levels of CKMB (in the range of 0.62–33.2 mg/L). Of the eighteen ischemic patients, two patients (P2, P3) who had high CKMB mass levels did not have abnormally high levels of SPH. One patient (P2) had a serum SPH level (120 pmol/mL) that was only moderately higher than the average of the age-matched controls, but had high levels of CKMB (33.2 mg/L) and CK (810 U/L), indicative of AMI. The other patient (P3) displayed a negligible level of serum SPH (18.1 pmol/mL), a normal CK level (161 U/L) and a high CKMB level (18.4 mg/L). The moderate-to-low SPH levels detected for these two patients represent a 11% false negative rate (2 of 18), because both patients were considered ischemic based on other indicators. The inclusion of the SPH data for these two patients (P2 and P3) in the AMI group also accounts for the somewhat lower SPH levels in the AMI group. (587±7 pmol SPH/mL), compared to the SPH levels for the ischemic patients undergoing coronary angioplasty (885±123 pmol/mL).

Based on the results obtained with the AMI patients tested, a relatively high serum SPH level is an effective early indicator of ischemia. This was further confirmed by the results obtained in the following individual studies.

Three Case Histories

Case History No. 1

Patient T2 was a 47 year-old female who presented herself to the emergency room of a hospital with complaints of angina Blood samples were drawn and the patient was then referred to a hospital's exercise stress test facility. The patient passed the treadmill test, showing no evidence of cardiac ischemia or AMI as detected by an ECG administrated during the stress test and by serum enzyme levels analyzed during her period of evaluation in the hospital. The patient was discharged from the hospital, but returned three weeks later with evidence of an AMI as determined by high serum levels of CK and CKMB and other clinical symptoms.

Analysis of this patient's serum SPH demonstrated that, at the time of her first visit to the emergency room, she had a very high level of SPH (810 pmol/mL). When she returned to the hospital with an AMI, her SPH level was even higher (greater than 1200 pmol/mL). Thus, the serum SPH level was an early indicator of ischemia and more predictive of her cardiac condition than the exercise stress test or the serum CK and CKMB analysis, both of which showed no evidence of cardiac ischemia or AMI on her first visit to the emergency room.

Case History No. 2

Patient MI-12 was a male who was admitted to the hospital with a confusing clinical presentation. When admitted, his CK level (126 U/L) was normal, but his CKMB level (3.8 mg/L) was elevated. His serum SPH level at admission was also high (732 pmol/mL), indicating ischemia. At about five hours after admission, this patient had an AMI. This result shows that the serum SPH level, but not by the CK parameter, accurately detected his ischemic condition. Thus, the results of the SPH test, alone or combined with the CKMB parameter, were predictive of imminent AMI.

Case History No. 3

This patient was a 58 year-old female who was admitted to the hospital for an initial evaluation of her heart condition. During the initial evaluation, blood was drawn and the serum showed normal CKMB (0.632 mg/L) but moderately high SPH (300 pmol/mL). Four days later she received a coronary bypass. After alleviation of the ischemia as a consequence of the bypass procedure, her serum SPH level was significantly reduced to 7.31 pmol/mL, whereas her serum CK (934 U/L) and CKMB (88.9 mg/L) levels remained high. This is consistent with SPH being an accurate indicator of ischemia, and the enzymes CK and CKMB being indicators of myocardial damage (i.e., large molecular weight cytoplasmic proteins that are released from necrotic myocardial cells). Thus, detection of elevated levels of serum SPH is an early diagnostic of ischemia or hypoxia because it is produced by cardiomyocytes before significant cell necrosis has occurred.

These results show that serum SPH is more predictive of the early stages of ischemia and imminent AMI than current methods generally used in diagnosis. Moreover, serum SPH is quantitatively related to the early events that precede cardiac cell death, in contrast to other biochemical markers (e.g., CK, CKMB and troponin) that are released after cell death. Thus, routine screening of patients for serum SPH can aid in the early diagnosis of coronary artery disease and identification of patients at high risk of heart disease who can be treated to prevent AMI. Quantitative detection of a single sphingolipid such as SPH, however, may be subject to variability which can be minimized by combining the measurement with detection of serum TNFα a to provide a more general index of risk of cardiac ischemia or hypoxia.

Example 2

In vitro Sphingosine Production from Cardiac Tissue Under Ischemic Conditions

To demonstrate that cardiac ischemia results in excess SPH production, tissue levels of SPH were examined in adult rabbit hearts subjected to retrograde coronary perfusion with hypoxic (ie., low oxygen) conditions (95% $CO_2$; 5% $O_2$) or with normal Krebs buffers (containing 5% $CO_2$; 95% $O_2$). The hearts were removed, quickly homogenized, and sphingolipids were extracted and detected as described above.

HPLC analysis of the extracts revealed significant increases (20-fold) in tissue SPH levels for hearts perfused with buffer containing 95% $CO_2$ when compared to control conditions. Moreover, these increases occurred after only 5 min. of treatment.

SPH is a cationic amphipathic lipid that can partition into whole blood and other body fluids. Therefore, the relative amounts of SPH were determined in whole blood and serum obtained from humans, rats, and rabbits. SPH was found predominantly in the serum, the preferred body fluid for measuring SPH levels for detecting cardiac ischemia or hypoxia.

In order to determine the time-dependent stability of SPH in serum, a human serum sample was obtained and allowed to sit at 22° C. for 5 hrs before sphingolipid and HPLC analysis. Serum samples were also spiked with commercially available SPH and similarly stored at room temperature. Neither the aged control serum samples nor the spiked samples showed appreciable differences in SPH levels compared to samples that were assayed immediately after collection or preparation of the spiked samples, indicating that SPH does not undergo degradation if serum samples were not assayed immediately after collection.

Example 3

Myocardial Risk Factor (MRF)

Serum levels of TNFα also increase in cardiac ischemia and correlate with the serum SPH levels detected in angioplasty patients. The product of these two parameters (e.g., the levels of a non-polypeptidic cardiac marker and a secondary [or tertiary] cardiac marker) is referred to as a "myocardial risk factor" (MRF) and is a useful quantitative indicator of an individual's possibility of injury resulting from myocardial ischemia. Because MRF can be calculated using different cardiac markers, it is important that the markers used in a particular MRF be specified.

Here, TNFα was measured using standard methods in an enhanced ELISA double antibody capture assay (using a Quantikine HS kit (Cat No. HSTA50) kit, R+D Systems, Minneapolis, Minn.). Human serum samples (200 $\mu$L) were assayed and compared to recombinant human TNFα standards using the assay procedures provided by the manufacturer.

Serum TNFα and SPH levels were determined from samples taken from the pulmonary artery of a patient (A5) experiencing the periodic ischemia (e.g., during balloon inflation) and reperfusion (e.g., when the artery is cleared) that occurs during successful angioplasty. Serum TNFα and SPH levels were both elevated prior to initiation of the angioplasty procedure (from =20 min to 0 min), Neither the TNFα nor the SPH increased during the ischemic period. They were already high and went down after reperfusion. Both TNFα and SPH parameters showed a biphasic response, with initial decrease after angioplasty followed by a steady rise back to pre-angioplasty levels. The time courses were similar with TNFα levels falling slightly ahead of SPH in time. This is consistent with TNFα being the trigger for SPH production.

Similarly, serum TNFα levels were assessed for 19 patients undergoing coronary angioplasty and for seven AMI patients. For comparison, serum TNFα levels were determined for two control groups (age-matched controls and healthy military personnel). Serun TNFα levels were highest in the AMI patients (5.2±0.6 pg/mL), and somewhat lower in the pulmonary artery blood taken from the angioplasty group before the procedure was done (3.6±0.74 pg/mL). The patients had significantly higher serum TNFα levels (4.04±0.57 pg/mL) compared to those of the age-matched control group ("Controls") of 2.43±0.32 pg/mL, and the healthy military subjects ("Athletes") of 1.22±0.29 pg/mL.

By comparing the results, it can be seen that serum TNFα levels showed the same trends as seen for the serum SPH levels in the three groups' tests. That is, the athletes had the lowest levels of SPH and TNFα, the age-matched controls had higher levels of SPH and TNFα, and the patients had the highest levels of SPH and TNFα. Therefore, a more accurate measure of on-going myocardial ischemia can be obtained by combining two or more parameters, e.g., the levels of a non-polypeptidic and a secondary or tertiary cardiac marker trending in the same direction, to calculate a MRF. When SPH is the non-polypeptidic cardiac marker and TNFα is the secondary cardiac marker, the MRF is the product obtained by multiplying the numerical value of the serum TNFα level and the numerical value of the serum SPH level.

Representative MRF data (using SPH and TNFα levels) for all ischemic patient groups in this experiment were combined and compared to age-matched and healthy military controls. The MRF of the ischemic patients (2820) was about 12-fold higher than that of the age-matched control group (238) and about 440-fold higher than that of the healthy military group (6.3). Thus, the MRF value distinguished ischemic patients from controls to a greater extent than did either serum SPH or serum TNFα measurement alone. Moreover, the calculated MRF value reduced the occurrence of false negatives for either parameter alone.

Table 1, below, shows the SPH/TNFα MRF value calculated for seven patients. The values were calculated by multiplying the SPH value (approximated to the nearest whole integer) and the TNFα value (approximated to the nearest one-tenth) to produce the MRF value (to the nearest whole integer). Six of the seven angioplasty patients had a MRF in the range of about 1,800 to about 3,000 range. The mean MRF value for these six patients was 2,326. Only one patient had a MRF outside of that range (patient A1 with MRF of about 16,000). The mean MRF for all seven patients is shown in Table 1. Based on the MRF values of the majority of the patients for whom the calculation was made, patient A1 appeared to have an atypically high level of ischemia, with the TNFα level being significantly higher than that of the other six patients. If the SPH level of patient A1 is multiplied by the mean TNFα value of the other six patients (2.9), the MRF value would be 3,254 which is close to the range seen for the other six patients.

TABLE 1

| Patient | SPH (pmol/mL) | TNFα (pg/mL) | MRF | CK (U/mL) |
|---------|---------------|--------------|-------|-----------|
| A1      | 1,122         | 14.4         | 16,157 | 175      |
| A4      | 868           | 2.9          | 2,500 | 110       |
| A5      | 1,000         | 2.7          | 2,700 | 50        |
| A6      | 582           | 3.2          | 1,845 | 33        |
| A8      | 772           | 3.1          | 2,393 | N/A       |
| A10     | 1,404         | 1.9          | 2,668 | 41        |
| A11     | 447           | 4.1          | 1,833 | 54        |
| Mean:   | 8851          | 4.6          | 4,302 | 77        |
| S.D.:   | 325           | 4.4          | 5,240 | 55        |
| S.E.:   | 133           | 1.8          | 2,139 | 25        |

There were no false negatives for the SPH value detected in the angioplasty group; showing that an elevated serum SPH level is an accurate predictor of ischemia Serum SPH was predictive of the early stages of ischemia and imminent AMI more frequently than other currently used methods, although false negative results were detected with a few AMI patients. Moreover, the level of SPH detected provides a quantitative measurement of early events that precede cardiac cell death. In contrast, other biochemical markers (e.g., CK and CKMB) appear to be more indicative of later events subsequent to cardiac cell death. Because measurement of serum SPH provides information on the level of cardiac ischemia even in the absence of other clinical indicators, the assay is also useful for monitoring the efficacy of cardiac treatments (e.g., bypass surgery or angioplasty). Testing of serum SPH levels is useful as a routine diagnostic of cardiac ischemia and hypoxia, permitting patients at risk of heart disease to be identified and treated. The method is also useful for monitoring patients during or after treatment for cardiac conditions to detect the level of cardiac ischenia or hypoxia as an indicator of the success of the treatment.

Although the results used to calculate the MRF presented above were based on HPLC-detection of SPH and ELISA detection of TNFα, it will be appreciated by those skilled in the art that a variety of assays can be used to detect any of the diagnostic sphingolipids and TNFα. Preferably, a kit that includes assays for TNFα and sphingolipids is used to provide a measure of the MRF. For example, anti-TNFα and anti-SPH antibodies/or an enzyme assay for sphingolipids are combined in a kit to assess the MRF value. For example, known biosensor technology can be used for the determination of two or more analytes in blood or serum. An algorithm may be used in the kit to calculate the MRF value, which may be particularly advantageous for detecting all three important sphingolipids, SPH, S1P and SPC, as well as TNFα, and determining a series of M values for all of the combinations of sphingolipid and TNFα, or for determining a single MRF value that is the product of all the measured sphingolipid levels and the TNFα level.

Example 4

TNFα Associated with Ischemia is Produced by Heart Cells

To demonstrate the myocardial cell origin of TNFα, both neonatal and adult rat cardiomyocytes in culture, devoid of fibroblasts and endothelial cells, were tested for production of TNFα.

Neonatal ventricular myocytes were dissociated from hearts obtained from one to four day old Sprague-Dawley rats essentially as described previously (Shields et al., *J. Biol. Chem.* 263:12619–12618, 1988). Ventricles were finely minced and dissociated with 0.5 g/L trypsin, 0.2 g/L EDTA in a calcium-free and magnesium-free Hank's buffered salt solution (Sigma, St. Louis, Mo.). The tissues were agitated, pelleted gently by centrifugation and the trypsin digestions were repeated five times. The supernatants containing cells in suspension were combined with DMEM/F 12 medium, filtered through 125 μm nylon mesh, and the filtrate was centrifuged. The pelleted cells were resuspended in DMEM/F12 medium and plated on fibronectin-coated glass coverslips in DMEM/F12 medium plus 10% fetal calf serum (FCS).

Freshly dissociated adult ventricular myocytes were prepared from hearts of adult (200 to 350 g) Sprague-Dawley rats by enzymatic dissociation using a Langendorff retrograde aortic perfusion apparatus. After perfusing the hearts with collagenase (Type II, Worthington Biochemicals, Freehold, N.J.), rat ventricles were diced and incubated for 30 min at 37° C. in 10 to 15 mL of 0.58 mg/mL collagenase in oxygenated Tyrode's solution (140 mM NaCl, 5.4 mM KCl, 5.0 mM $MgCl_2$, 1.0 mM $CaCl_2$, 10 mM HEPES, 0.25 mM $NaH_2PO_4$, pH 7.3). The dissociated myocytes were plated on laminin-coated (50 μg/mL) culture dishes and cultured for 18 hr in DMEM/F12 plus 10% FCS, in the presence or absence of the test agent (e.g., LPS or control buffer).

The results showed these cells were capable of secreting high amounts of TNFα in response to the bacterial endotoxin, LPS, which is a well-known secretagogue for the cytokine. The amount of secreted TNFα can reach about 1500 pg/mL which is within the range of TNFα capable of producing significant apoptotic cell death in cardiomyocytes. Additionally, in vitro experiments with cultured rat cardiomyocytes stimulated by LPS show that a significant amount of SPH (700 pmol/mL) is, also secreted from the cells. These results demonstrate that heart cells are a source of secreted SPH as well as TNFα. Further, these in vitro results are consistent with the in vivo results in which TNFα and SPH levels in the pulmonary arteries of human subjects undergoing balloon angioplasty were greater than the serum levels of TNFα found in the femoral veins of the same patients. The data indicate that the TNFα levels in the pulmonary artery of coronary angioplasty patients correlated well with changes in pulmonary artery SPH levels during the same treatment. Both the in vitro and in vivo data indicate that the elevated serum TNFα and SPH levels'seen in myocardial ischemia (e.g., during coronary angioplasty) likely results from TNFα released by ischemic heart cells into the circulation.

The elevated serum SPH levels detected in the ischemic patients was not produced by skeletal muscle ischemia as demonstrated by assaying serum samples from healthy athletes and military personnel before and after inducing severe skeletal muscle ischemia. The subjects exercised to exhaustion on treadmills placed in a room having an ambient temperature of 49° C. to induce skeletal muscle ischemia which was confirmed by measuring serum lactate. Prior to the exercise regime, serum SPH averaged 4.18±4.5 pmol/mL, which slightly decreased to 4.02±3 pmol/mL after exercise. These serum SPH values were substantially lower than those detected in ischemic patients. Importantly, serum TNFα levels were not increased in these subjects undergoing severe skeletal muscle ischemia (for example, serum TNFα values for the military personnel were 1.22±0.49 pg/mL before exercise and rose insignificantly to 1.39±0.23 pg/mL after exercise).

Example 5

Use of Anti-sphingolipid Antibodies to Detect Sphingolipids in Whole Blood or Serum Anti-sphingolipid (or other non-polypeptidic cardiac markers) monoclonal antibodies (mAb), e.g., mAbs reactive against SPH, S1P, SPC, and DHSPH, are prepared by methods similar to those used in the preparation of anti-phospholipid antibodies. Briefly, one method of mAb production involves direct immunization of sphingolipid-coated, acid-treated Salmonella. Minnesota directly into a mouse spleen using known methods used to make anti-phospholipid mAbs (Reza et al., *FEBS Lett.* 339:229–233, 1994; Umeda et al., *J. Immunol.* 143:2273–2279, 1989). For production of anti-SPH antibodies, the acid-treated *S. Minnesota* is coated with the desired sphingolipid, e.g., SPH, and injected into the mouse spleen prior to cell fusion to produce a hybridoma that secretes anti-SPH mAb. Similar methods are used to produce anti-S1P mAb and anti-SPC mAb. Alternately, fatty acid free BSA-sphingolipid conjugates can be used as the immunogen in order to present unique epitopes to the animal. Care must be taken to ensure that mAbs are not produced to oxidized lipid or protein-lipid adducts. [see discussion by Witztum et al. in refs. (Horkko et al., *J. Clin. Invest.* 98:815–825, 1996; Palinski et al., *J. Clin. Invest.* 98:800–814, 1996)].

The mAbs are initially used to detect the specific ligand in any of a variety of standard immunoassays, such as, for example, an enzyme-linked immunosorbent assay (ELISA), a radioimmuno assay (RIA), by direct labeling of the mAb with a calorimetric label (e.g., colloidal gold or latex beads), or by indirect labeling of the mAb such as in a sandwich immunoassay. All of these assays are well known in the art and can be practiced by the skilled artisan with minimal routine testing to determine optimal conditions for detecting the specific ligand(s). Preferably, the immunoassay would employ the standard lateral flow-through format or biosensor technology.

Lateral flow formats involve double capture antibody technology where the analyte in the blood sample is captured by the first antibody tethered to the substrate. A strept-avidin system is then used to detect binding of the second antibody.

Biosensor technology typically uses surface plasmon resonance to detect refractive index changes on the surface of a gold/glass matrix as the antigen (e.g., the sphingolipid) binds to the tethered antibody (e.g., anti-SPH) [see for example, Kuziemko et al., *Biochem.* 35:6375–6384, 1996, where cholera toxin binding to gangliosides, including lactosyl ceramides, was studied]. Biosensors are preferred because they are very rapid (develop in minutes), quantitative, and are amenable to use with multiple ligands. Algorithms and digital readouts are possible with biosensors. Biosensor format-based immunoassays for detection of SPH, S1P, and SPC can be performed individually, to provide independent measurements of each of the sphingolipids as indicators of ischemic cardiac conditions. Alternatively, a single assay could include multiple mAbs to provide a single measurement of any combination of sphingolipids (e.g., SPH and S1P; SPH and SPC; S1P and SPC; or SPH, S1P and SPC), alone or in combination with one or more other markers, e.g., TNFα.

Example 6
Enzymatic Assay for Serum or Whole Blood Sphingosine

This method involves purification of sphingosine kinase and its use in a coupled assay employing pyruvate kinase and its substrate phosphoenopyruvate to detect ATP hydrolysis. The product of the coupled reaction is pyruvic acid and the resulting change in pH is used in a kit that takes advantage of pH-dependent polymer breakdown technology (as described in Serres, A. et al., *Pharmaceutical Res.* 13(2):196–201, 1996) and the subsequent changes in impedance that are measured. Sphingosine kinase is isolated from Swiss 3T3 cells or other cells as previously described (Olivera A., et al., *Anal. Biochem.* 223(2):306–312, 1994).

The assay includes the following features: The substrate of the test strip is coated with a pH-sensitive linear terpolymer (e.g., a derivative of poly(N-isopropylacrylamide-co-burylmethacrylate-co-acrylic acid). A blood or serum sample is dropped onto the test strip and the coupled reaction precedes. As the pH drops by the coupled enzyme assay (the decrease in pH is proportional to the amount of SPH in blood), the polymer breaks down and exposes the conductor on the test strip. An impedance measurement is then made which is proportional to the amount of SPH in the blood or serum sample that was dropped onto the strip.

Example 7
Phage Display Assay for Sphingolipid Receptor Isolation

This technique is used to screen phage which encode receptors which bind with high affinity to the markers, particularly the non-polypeptidic cardiac markers, of the invention, and express them on their surfaces. See U.S. Pat. Nos. 5,223,409 and 5,403,484 for a detailed description of phage display technology. Bacteria, which express the receptor, are then cloned and used in a biosensor-based kit. This technique can be used to detect the markers used in the practice of this invention, including all important sphingolipids, including SPH, S1P, DHSPH, and SPC. Because the techniques used to isolate receptors for any marker are substantially the same, the techniques are described generically herein. This method is described in more detail in McGregor, D., *Mol. Biotech.* 6(2):155–162, 1996.

Typically, a cDNA library is provided (e.g., a cDNA library that is available from a number of commercial sources, including Clontech, San Diego, Calif.) and then used to create fusion proteins with a membrane protein of a filamentous male phage such as M13. Phage clones expressing the fusion protein containing the receptor for the desired marker, e.g., SPH are detected and isolated using standard ligand binding assays. The gene for the receptor is then excised from positive clones using standard endonuclease restriction enzymes and cloning methods (see, e.g., J. Sambrook, *Molecular Cloning, A Laboratory Manual,* 2nd Ed., CSH Lab. Press, 1989). The gene may also be expressed in a bacterial system using standard methods to yield unlimited quantities of the receptor. The receptor is purified using standard methods and is then used to detect the marker for which the receptor demonstrates specificity. For example, the purified receptor is tethered to an ELISA plate, to a Biacore dextran surface, to a test strip of any of a number of detection kits, to biosensor detectors and the like, and used to measure the quantity of a sphingolipid in the blood or serum. Other applications taking advantage of marker binding to its membrane receptor are also envisioned.

Example 8
Measurement of Anti-sphingosine Antibodies in Human Blood

This method is based on the assumption that patients experiencing ischemia produce anti-sphingolipid antibodies as a consequence of elevated blood levels of sphingolipids such as sphingosine. It is also based on the findings that anti-lactosylsphingosine antibodies have been observed in patients with colorectal cancer (Jozwiak W. and J. Koscielak, 1982) and anti-galactocerebrosides were detected in the sera of leprosy patients (Vemuri N. et al., 1996).

The potential antigenicity of sphingosine and its metabolites is suggested by their structures as a cationic amphiphiles (e.g., see FIG. 1) and by the finding that antibodies can be generated against phospholipids (Umeda M. et al., 1989) and glycosphingolipids (Vemuri N. et al., 1996). For example, anti-glycosphingolipid antibodies were detected in the serum of calves experimentally infected with *T. saginata* (Baumeister S. et al., *Parasitol. Res.* 81:18–25, 1995). This technique can be applied to detecting any sphingolipid or sphingolipid metabolite, including SPH, DHSPH, S1P and SPC, as well as other non-polypeptidic cardiac markers used in the practice of this invention.

To isolate antibodies against non-polypeptidic cardiac markers, e.g., SPH, from the serum of ischemic patients, one can employ affinity purification of the antibodies from the serum using a matrix, such as Sepharose, to which the marker to be detected is conjugated. These antibodies form the basis of an immunological test, using any of a variety of well-known immunological screening methods, that would be easy to administer and inexpensive to perform for large patient screenings.

Example 9
Home Monitoring of Cardiac Markers

Individuals who wish to monitor their cardiac marker levels without the aid of a health care professional may use a home monitoring device. Finger stab dipstick technology is widely used for blood glucose monitoring and this method can be adapted to the measurement of blood-borne cardiac markers (e.g., non-polypeptidic, secondary, and tertiary markers) in a drop of blood, given the disclosure herein. The cardiac markers used in the practice of the invention, including sphingosine and its derivatives, can also be measured in many tissues and body fluids besides blood, including saliva, sweat, and urine. Other home monitoring devices useful in the practice of this invention include those analogous to in-home pregnancy tests, where the level of a particular marker or set of markers is measured in urine.

A portable electronic measurement device can also be applied in the practice of this invention. For instance, a wrist-worn device similar in size and shape to a wristwatch has been developed for monitoring blood sugar levels in diabetics. For example, the Cygnus GlucoWatch™ platform allows an individual to continuously monitor glucose through intact skin for more accurate assessment of the analyte at all times and without the discomfort of the finger stab technique. Similarly, real-time continuous or periodic monitoring of one or more cardiac markers in accordance with the instant methods could be accomplished by wristwatch platforms. In such embodiments, the measurement of non-polypeptidic cardiac markers (and secondary and tertiary markers, if desired) according to the invention would occur directly through the skin, and would be compared with marker levels indicative of cardiac conditions associated with ischemia, hypoxia, and others correlating with various forms of heart failure. Downloading of stored data from such a device having data logging capability is also envisioned, and would provide the clinician with a record of the patient's recent history of marker level changes.

Furthermore, such a device, or other home monitoring device designed to monitor cardiac marker levels according to the invention, can be used in conjunction with an alarm system that is activated when one or more cardiac marker level (or a calculated index such as MRF) exceeds a certain threshold. The alarm may inform the patient, i.e., wearer, or a third party, e g., a friend or relative,, a health care professional, or emergency response personnel, such as the police, paramedics, or the fire department of a change in the level of the marker(s) being monitored. Such an alarm, when transmitted, may also include telemetry.

A home monitoring device according to the invention will preferably be accompanied by instructions for use. The device may also be accompanied with a notice in form prescribed by a governmental agency regulating the manufacture, use, or sale of medical devices, which notice is reflective of approval by the agency of the form of the device for home use. Such notice, for example, may be the labeling approved by the U.S. Food and Drug Administration, or the equivalent governmental agency in other countries, for medical devices, or the approved product insert.

Example 10
Sphingolipids as Inhibitors of Protein Kinase C

This embodiment of the invention employs a coupled assay to assess sphingosine levels in blood or other tissues or bodily fluids by taking advantage of the ability of sphingosine and other lysosphingolipids to inhibit protein kinase C (PKC) (Hannun and Bell, *Science* 234:670–674, 1987; Hannun et al., *J. Biol. Chem.* 261:12604–12609, 1986). The amount of sphingolipid in the blood sample is quantitatively related to the change in absorbance at 340 nm as a stoichiometric amount of NADH is oxidized by the coupling system as described by Sabbadini and Okamoto (Sabbadini and Okamoto, *Arch. Biochem. Biophys.* 223:107–119, 1983).

It has been shown that sphingosine inhibits PKC by preventing DAG binding to the enzyme (Faucher et al., *J. Biol. Chem.* 263:5319–5327, 1988). Thus, sphingosine may bind directly to PKC via the DAG binding site. The sequence for PKCα and its consensus DAG binding site is known (Hurley et al., *Protein Science* (6):477–80, 1997). Since SPH can also bind to putative sites on sphingosine kinase and other proteins with which is specifically interacts, it quite likely that several proteins have specific SPH binding sites. Accordingly, the putative sphingplipid binding site can be cloned using standard techniques, after the screening of phage display libraries (see above) for colonies, which express the sphingolipid recognition site. Expression cloning of the cDNA of this protein would produce a reagent that could be used in a standard ELISA to detect sphingolipid changes in a blood sample.

One skilled in the art will readily appreciate that the present invention is well adapted to carry out the objects and obtain the ends and advantages mentioned, as well as those inherent therein. The methods, procedures, treatments, devices, and compositions described herein are presently representative of preferred embodiments, are exemplary, and are not intended as limitations on the scope of the invention. Upon reading this specification, changes therein and other uses will occur to those skilled in the art, each of which is encompassed within the spirit of the invention as defined by the attached claims.

All patents and publications referred to above are herein incorporated by reference to the same extent as if each individual publication was specifically and individually indicated to be incorporated by reference.

The invention illustratively described herein suitably may be practiced in the absence of any element or elements, or limitation or limitations, which is not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims. Other embodiments are within the following claims.

I claim:

1. A kit for detecting a condition which causes heart disease in a mammal, the kit comprising a composition for detecting a level of at least one non-polypeptidic cardiac marker in a test sample obtained from said mammal, wherein said kit is able to determine if said level of said non-polypeptidic cardiac marker in said test sample correlates with said condition that causes heart disease in a mammal wherein said marker is selected from the group consisting of sphingolipid, sphingosine, sphingosine-1-phosphate, dihydrosphingosine and sphingosylphosphorylcholine.

2. A kit according to claim 1 wherein said level of at least one non-polypeptidic cardiac marker is measured quantitatively.

3. A kit according to claim 1 wherein said composition comprises a substrate.

4. A kit according to claim 3 wherein said substrate is an antibody which binds specifically to a non-polypeptidic cardiac marker.

5. A kit according to claim 3 wherein said substrate is an antibody which binds specifically to a sphingolipid.

6. A kit according to claim 1 wherein said kit comprises one or more standards having a predetermined level of a non-polypeptidic cardiac marker.

7. A kit according to claim 6, wherein said kit comprises two or more standards, wherein at least two of said standards have different levels of said non-polypeptidic cardiac marker.

8. A kit according to claim 7 wherein said kit comprises instructions for comparing the level of said non-polypeptidic cardiac marker in said test sample to the level of at least one non-polypeptidic cardiac marker in said two or more standards.

9. A kit according to claim 1 wherein said kit comprises a composition or device for obtaining a test sample using an invasive method.

10. The kit according to claim 1 further comprising a composition for measuring the level of a second marker.

11. The kit according to claim 10 wherein said second marker is a pro-inflammatory cytokine.

12. The kit according to claim 11 wherein said pro-inflammatory cytokine is TNFα.

13. A method of using the kit of claim 1 to detect a condition which causes heart disease in a mammal.

14. The kit of claim 1 wherein said heart disease is selected from the group consisting of heart failure, cardiac ischemia and cardiac hypoxia.

15. The kit of claim 14 wherein said heart failure is selected from the group consisting of acute myocardial infarction, myocarditis, a cardiomyopathy, congestive heart failure and idiopathic heart failure.

16. The kit of claim 1 wherein said mammal is a human.

* * * * *